(12) United States Patent
Kontiola

(10) Patent No.: US 8,998,810 B2
(45) Date of Patent: Apr. 7, 2015

(54) ARRANGEMENT IN A TONOMETER

(75) Inventor: Antti Kontiola, Helsinki (FI)

(73) Assignee: Tiolat Oy, Helsinki (FI)

( * ) Notice: Subject to any disclaimer, the term of this patent is extended or adjusted under 35 U.S.C. 154(b) by 2058 days.

(21) Appl. No.: 11/722,079

(22) PCT Filed: Dec. 14, 2005

(86) PCT No.: PCT/FI2005/000530
§ 371 (c)(1),
(2), (4) Date: Aug. 20, 2009

(87) PCT Pub. No.: WO2006/067266
PCT Pub. Date: Jun. 29, 2006

(65) Prior Publication Data
US 2009/0306493 A1    Dec. 10, 2009

(30) Foreign Application Priority Data

Dec. 21, 2004  (FI) .................................... 20041641

(51) Int. Cl.
*A61B 3/16*   (2006.01)

(52) U.S. Cl.
CPC .................... *A61B 3/16* (2013.01)

(58) Field of Classification Search
CPC .................. A61B 3/16; A61B 3/165
USPC ................................... 600/399–406
See application file for complete search history.

(56) References Cited

U.S. PATENT DOCUMENTS

| 5,671,737 | A * | 9/1997 | Harosi | 600/405 |
| 6,093,147 | A * | 7/2000 | Kontiola | 600/405 |
| 6,423,014 | B1 * | 7/2002 | Churchill et al. | 600/587 |

FOREIGN PATENT DOCUMENTS

| JP | 5056932 | 3/1993 |
| JP | 10504749 | 3/1996 |
| JP | 2000014643 | 1/2001 |
| JP | 2002112967 | 4/2002 |
| JP | 2005529671 | 12/2003 |
| WO | 03105680 | 12/2003 |

* cited by examiner

*Primary Examiner* — Adam Eiseman
(74) *Attorney, Agent, or Firm* — Fasth Law Offices; Rolf Fasth

(57) ABSTRACT

The arrangement in a tonometer has a probe that is brought into contact with the surface of the eye and the intraocular pressure in the eye is derived from the variations in the velocity of the probe. The probe is formed of a piece of a non-magnetic substance. The arrangement includes a holder located in the tubular component and attached to a shaft providing the force for the measurement, in which holder there is a guiding means for guiding a movement of the probe along an internal surface of the tubular component.

13 Claims, 1 Drawing Sheet

ARRANGEMENT IN A TONOMETER

The present invention relates to an arrangement in a tonometer and more specifically to an arrangement concerning the measuring head in the tonometer, in which a probe is brought into contact with the surface of the eye at a specific velocity.

There are quite many different basic constructions in tonometers. Most of them are difficult to use and inaccurate, while their construction is quite primitive. Recently, however, tonometers have also been developed, which are quite easy to use, very accurate, and hygienic in all respects.

One such type of tonometer is disclosed in Finnish patent 109269, the inventor of which is also the inventor of the present application. The general type of the tonometer is one, in which a lightweight probe is made to move from the device and impact the surface of the eye, the movement of the probe and the changes in it being registered and the intraocular pressure being calculated from the data recorded.

For reasons of hygiene, the probe in the device according to the aforementioned patent is disposable and its formed of a probe tip and a shaft of a magnetic material, which extends to the area of the coils or similar devices inside the device. Such a solution is relatively expensive to use.

The present invention is intended to make the probe less expensive and thus create a simple and cheap probe solution. This and other benefits and advantages of the invention are achieved in the manner stated to be characteristic in the accompanying Claims.

Figure 1:
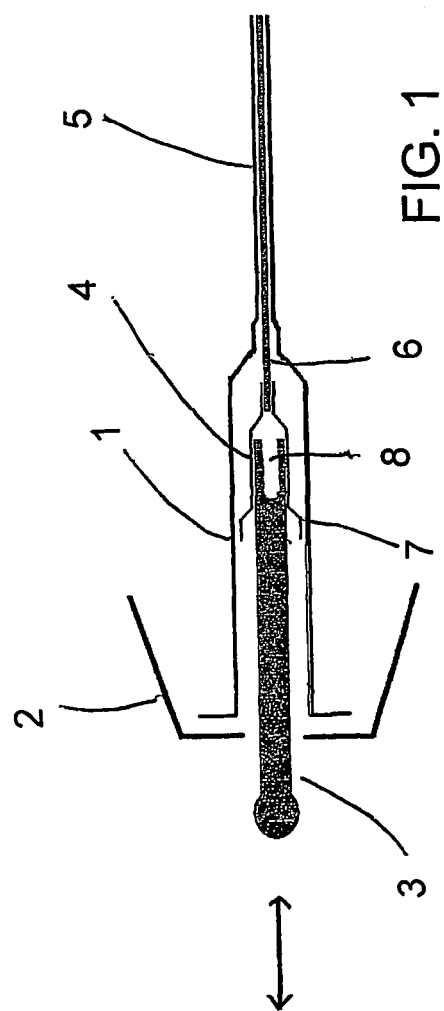

In the following, an arrangement according to one embodiment of the invention is examined in greater detail with reference to the accompanying patent drawings, in which FIG. 1 shows a cross section of one arrangement according to the invention; while FIGS. 2a and 2b show detailed views of one component of the arrangement according to the invention, seen from two different directions.

Thus, FIG. 1 shows a component of the tonometer according to the invention. The component is located in the tonometer close to the eye and in it there is a probe 3, which is shot toward the eye, the intraocular pressure being calculated from the movements of the probe, or the variations in the movements. The movement is created in a conventional manner magnetically with the aid of coils, which are not shown here, and of a rod/wire 6 of magnetic material, which goes inside the coil. Of course there are other ways to create the movement.

Whereas the entire probe according to the prior art forms a single piece and as such is relatively long and difficult to handle and is also expensive, the present invention incorporates the realization that the probe can be made as a two-part, easily exchangeable, and cheap construction. The drawings show an example of such a construction.

Thus, inside the tubular case 1 there is a holder 4, which is permanently attached to the shaft 6 of magnetic material described above. The shaft 6 is guided by being inserted into a thin tube that forms a single piece with the case-like component 1. The joint between the shaft 6 and the holder 4 can also be detachable, of course, if required.

Because the probe leaves the structure from relatively tight opening in the shield plate 2 in the front part of the device, there must be some way to ensure that the shaft of the probe 3 will not catch on the edges of the opening. As the forces used in the measurement are quite small, striking the edges of the opening will make the measurement result unreliable. The free travel of the probe 3 is ensured by making a flange 7 in the holder, which provides proper guidance. The material of the holder 4 is selected, relative to the material of the collar 1, to be such that the resistance arising from the mutual contact between these two components will be extremely small. It will therefore be insignificant in terms of the measurement result.

In the embodiment shown in FIG. 1, the retention of the exchangeable probe 3 in the holder 4 is ensured by a small spring force, which is caused by the shape of the end of the probe, so that when the probe is pushed into the holder, the split 8 end of the shaft will compress slightly.

After the intraocular pressure has been measured, the probe 3 is detached from the holder by simply pulling it outwards and a new one is correspondingly set in place.

Figure 2:
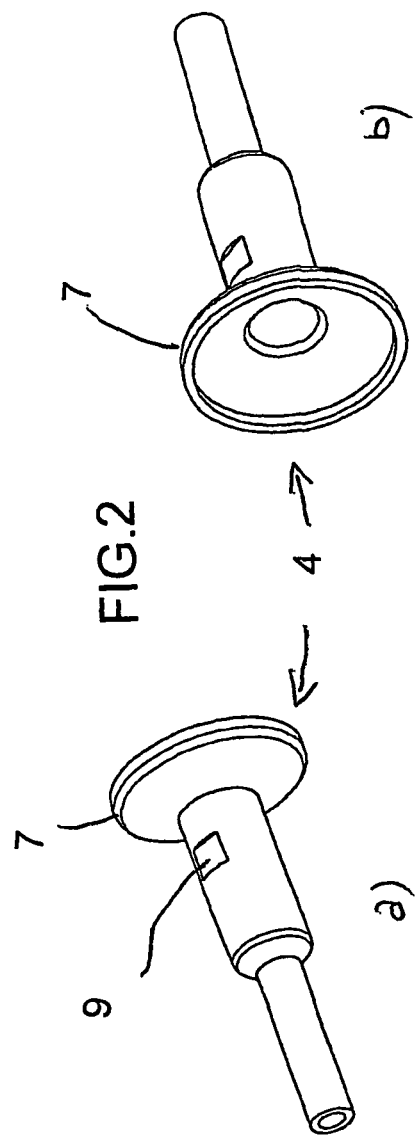

FIGS. 2a and 2b show an enlarged axonometric view of the holder seen from two directions. Compared to FIG. 1, the holder need not be described in greater detail. However, shows another simple alternative for holding the probe in the socket is shown in the holder 4 in FIG. 2. This is a small depression 9 in the body of the holder. This depression results in a small protrusion in the interior of the hollow holder, which compresses the probe sufficiently to hold it in place.

It is obvious that the invention is in no way restricted to the disclosed embodiment. The external appearance of the holder can differ greatly from that described. For example, instead of a unified flange 7, the guiding effect can equally well be created by using relatively thin 'whiskers', which extend essentially to the internal wall of the tube 1. Three whiskers, for example, will be quite adequate for guidance.

Many different solutions for holding the probe in place in the holder, which are not described here, can be found in various areas of technology.

The manufacturing material of the probe is always selected in such a way that, when it is applied to the measurement event according to the invention it will give a good result. However, it is highly probable that it will be appropriate to manufacture the probe from a plastic, the weight and hygienic requirements of which are suitable for this purpose.

The invention claimed is:

1. An arrangement in a tonometer, comprising:
   a probe contactable with a surface of an eye to derive an intraocular pressure in the eye from variations in a velocity of the probe, the probe having an end,
   the probe being at least partially disposed inside a tubular component having a channel defined therein,
   a holder located inside the channel of the tubular component and attached to a shaft inserted into the holder, the holder having holding means being in operative engagement with an end of the probe for holding the end and being adapted to provide a force to the probe for a measurement of the intraocular pressure in the eye, the end of the probe being compressed by an inside of the holder,
   the holder having guiding means for guiding a movement of the probe along an internal surface of the channel disposed inside the tubular component, and
   the probe, the holder and the shaft being movable between a retracted position and an extended position, the guiding means extending to the internal surface of the channel when the probe, the holder and the shaft being in the retracted position.

2. The arrangement according to claim 1 wherein the guiding means is formed of a flange-like part of the holder.

3. The arrangement according to claim 1 wherein the guiding means is a flange that is movable inside tubular component.

4. The arrangement according to claim 1 wherein the arrangement further has a biasing means for causing a spring force, in either the holder or at the end of the probe.

5. The arrangement according to claim 1 wherein both the probe and the holder are manufactured from a plastic material.

6. The arrangement according to claim 1 wherein the guiding means has whiskers that extend to an internal wall.

7. The arrangement according to claim 1 wherein the guiding means is a flange.

8. The arrangement according to claim 1 wherein the end of the probe is compressible against an interior surface of the holder.

9. The arrangement according to claim 8 wherein the end is a split end that is compressible when the split end is pushed into the holder.

10. The arrangement according to claim 1 wherein the holder has a depression defined therein.

11. The arrangement according to claim 10 wherein the holder has an opening defined therein and the depression extends into the opening to form a protrusion inside the opening.

12. The arrangement according to claim 11 wherein the protrusion compresses the probe inserted into the holder.

13. The arrangement according to claim 1 wherein the holder is disposed between the probe and the shaft and wherein one end of the holder is attached to an end of the shaft.

\* \* \* \* \*